(12) United States Patent
Rhodes

(10) Patent No.: US 10,788,460 B2
(45) Date of Patent: Sep. 29, 2020

(54) METHOD FOR FINGERPRINTING AND SORTING DIAMONDS

(71) Applicant: GEMOLOGICAL INSTITUTE OF AMERICA, INC. (GIA), Carlsbad, CA (US)

(72) Inventor: George Wyatt Rhodes, Corrales, NM (US)

(73) Assignee: Gemological Institute of America, Inc. (GIA), Carlsbad, CA (US)

(*) Notice: Subject to any disclaimer, the term of this patent is extended or adjusted under 35 U.S.C. 154(b) by 0 days.

(21) Appl. No.: 16/382,178

(22) Filed: Apr. 11, 2019

(65) Prior Publication Data
US 2019/0302060 A1 Oct. 3, 2019

Related U.S. Application Data

(63) Continuation of application No. 15/444,736, filed on Feb. 28, 2017, now Pat. No. 10,386,337.

(51) Int. Cl.
*G01N 29/12* (2006.01)
*G01N 29/24* (2006.01)
(Continued)

(52) U.S. Cl.
CPC .......... *G01N 29/12* (2013.01); *G01N 29/2437* (2013.01); *G01N 29/4454* (2013.01);
(Continued)

(58) Field of Classification Search
CPC .............. G01N 29/12; G01N 29/2437; G01N 29/4454; G01N 29/46; G01N 2291/0232; G01N 2291/102
(Continued)

(56) References Cited

U.S. PATENT DOCUMENTS 5,062,296 A * 11/1991 Migliori ................. G01N 29/12
73/579
5,495,763 A * 3/1996 Rhodes .................. G01N 29/12
73/579
(Continued)

FOREIGN PATENT DOCUMENTS

| CN | 104599392 A | 5/2015 | |
| WO | 2012/058842 A1 | 5/2012 | |
| WO | WO-2012058842 A1 * | 5/2012 | ............. G01N 29/46 |

OTHER PUBLICATIONS

WO-2012058842-A1 (Year: 2012).*
(Continued)

*Primary Examiner* — Peter J Macchiarolo
*Assistant Examiner* — Monica S Young
(74) *Attorney, Agent, or Firm* — DLA Piper LLP (US)

(57) ABSTRACT

Resonant Ultrasound Spectroscopy (RUS) is applied to diamonds (both cut/polished gemstones and rough diamonds) to yield a digital fingerprint from which the stone may be authenticated and sorted according to the structural quality. Diamonds are mined as rough stones from which they undergo examination to determine their value as being gem, or of two different industrial qualities. Fewer than 25% of mined diamonds are worthy of cutting and polishing to yield gems for jewelry. About 40% of the remaining population still have value as industrial diamonds for machine tools, and the rest is ground into dust to provide coatings for grinding applications. Rough stones exist in two conditions being coated and uncoated. The coated stones have a layer
(Continued)

of polycrystalline diamond, different from the predominant crystal structure, rendering them opaque. This interferes with optical inspection, as any cracks, or inclusions can't be seen. RUS provides a reliable sorting and fingerprinting system for both cut/polished stones as well as rough diamonds of sufficient structural quality to yield a spectral signature. As high value items, diamonds are shipped around the world, and but sometimes thefts occur. RUS yields a digital fingerprint allowing the identity of an individual stone to be verified upon recovery.

15 Claims, 5 Drawing Sheets

(51) Int. Cl.
    *G01N 29/46* (2006.01)
    *G01N 29/44* (2006.01)
(52) U.S. Cl.
    CPC ..... *G01N 29/46* (2013.01); *G01N 2291/0232* (2013.01); *G01N 2291/102* (2013.01)
(58) Field of Classification Search
    USPC .......................................................... 73/579
    See application file for complete search history.

(56) References Cited

U.S. PATENT DOCUMENTS

| | | | | |
|---|---|---|---|---|
| 5,922,956 | A * | 7/1999 | Rhodes | G01H 13/00 73/579 |
| 8,903,675 | B2 * | 12/2014 | Jauriqui | G01N 29/043 702/124 |
| 9,304,112 | B2 | 4/2016 | Rhodes et al. | |
| 2005/0117145 | A1 * | 6/2005 | Altman | G01N 21/87 356/30 |
| 2007/0005269 | A1 * | 1/2007 | Mitchell | G01B 11/162 702/35 |
| 2010/0207602 | A1 * | 8/2010 | Loverich | G01N 29/022 324/76.49 |
| 2013/0262894 | A1 | 10/2013 | Lee et al. | |
| 2014/0002203 | A1 * | 1/2014 | Liu | H03B 28/00 331/156 |
| 2014/0298911 | A1 * | 10/2014 | Rhodes | G01N 29/12 73/579 |
| 2015/0300993 | A1 * | 10/2015 | Prest | G01N 29/12 148/508 |

OTHER PUBLICATIONS

International Search Report and Written Opinion received for PCT Patent Application No. PCT/US2018/019956, dated May 14, 2018, 12 pages.

* cited by examiner

METHOD FOR FINGERPRINTING AND SORTING DIAMONDS

RELATED APPLICATION

This application is a continuation of U.S. patent application Ser. No. 15/444,736 filed on Feb. 28, 2017, now U.S. Pat. No. 10,386,337, which is hereby incorporated by reference in its entirety.

BACKGROUND

1. Field of the Invention

This invention relates to the nondestructive testing of diamonds both cut/polished and rough stones) to provide a digital fingerprint from which a stone may be identified and a quality measurement by which it may be sorted for potential value.

2. Brief Description of the Related Art

Diamonds are mined as rough stones from which they undergo examination to determine their value as a gem, or of two different industrial qualities. Fewer than 25% of mined diamonds are worthy of cutting and polishing to yield gems for jewelry. FIG. 1 illustrates a cut stone with a single crystal. FIG. 2 illustrates the display produced from an uncoated rough stone when more than 1 crystal is in the structure. FIG. 3 shows a similar stone, only coated. About 40% of the remaining population still have value as industrial diamonds for machine tools (FIG. 4), and the rest is ground into dust to provide coatings for grinding applications (FIG. 5). Rough stones exist in two conditions: coated and uncoated. The coated stones have a layer of polycrystalline diamond, different from the predominant crystal structure, rendering them opaque. This interferes with optical inspection, as any cracks, or inclusions can't be seen. A reliable sorting system would be of great use. As high value items, diamonds are shipped to processors in Antwerp, India, Hong Kong . . . , but sometimes the shipments are stolen. There is a need to fingerprint these stones, at their origin, that when recovered, their identity can be confirmed. Once a stone is cut and polished, there is a desire to fingerprint the object to ensure its integrity as it changes custody. Resonant Ultrasound Spectroscopy (RUS) fulfills these needs.

RUS was commercialized in the early 1990s and is the ideal method to verify the both the identity and structural integrity of a solid object. The resonances inherent in a solid object are dependent on the physical shape, density and elastic properties of the sample. The elastic properties, and density of cut diamonds are well characterized, but the shapes are highly variable. With rough stones, cracks are often present, which impact the structural rigidity, easily observable with RUS. This allows the application of RUS to produce a fingerprint unique to the cut/polished sample solely due to the physical shape including dimensions, and sort rough diamonds for the structural properties, while also providing a fingerprint for those with rigid structures.

As shown in U.S. Pat. No. 5,922,956; "Dynamic Ultrasonic Resonant Testing, Rhodes, Jul. 13, 1999, a solid object is excited by an exciting mechanical input (transducer) at a plurality of ultrasonic frequencies (the swept sine method), and sensing the resonant mechanical responses with the inverse process (1 or 2 mechanical receiving transducers). A dynamic signal analyzer is connected to receive the response of the sample and to output the resonance spectrum. A computer then determines the relevant resonances that adequately describe the spectrum, which can be stored as a digital fingerprint for a later comparison to identify a specific stone. In addition to the absolute frequency spectra, another method that is applied to fingerprinting an object uses differences Q (the quality of the resonance as defined as the full width at half maximum divided into the center frequency), as was first described in U.S. Pat. No. 5,495,763; Rhodes, et al. Mar. 5, 1996 entitled "Method for resonant measurement".

Q becomes an important factor in establishing a unique fingerprint, in that it defines the accuracy of the measurement. For example, cut, polished diamonds exhibit Q's on the order of 10,000. This means that a single resonance has 10,000 points that define a single resonance, yielding an accuracy of 1 in $10^4$. If we examine 2 diamonds with ostensibly the same size and shape, the probability that this first resonance will be exactly the same for the 2 stones is 1 in 10,000. If we use the first 2 resonances, the probability that both will be coincident becomes 1 in 100,000,000 ($10^4 \times 10^4$). Practically, if we record the first 3 resonances for all known polished diamonds, there becomes very little chance that any 2 diamonds can have the identical resonances.

Rough stones often contain cracks. When cut, the expert detects these flaws and is able to cut single crystals from the raw stone. The effect on the resonance spectrum is to substantially lower the Q by a factor of 10 or more (FIG. 4). If we observe a Q of 100, where we needed 2 resonances to have a probability of 1 in 100 million of have coincidence of frequencies in a polished stone, we would need 4 resonances to achieve a unique signature if a crack, or cracks were present. Since many resonances exist in a narrow bandwidth (like 10 between 1 MHz and 3 MHz for a 0.5 ct sample), we have several from which selections can be made. All stones with a reliable resonance structure can be fingerprinted. The accuracy of each resonance determines how many resonances are required to result in a reliable fingerprint.

Multiple crystals can exist in a single stone. In [0005] we cite 10 resonances being observable in a specified frequency range for a single crystal. When we observe twice, or 3 times that number (FIGS. 2 and 3), we know that 2, or more crystals are in that stone. This assists the examiner to value the diamond.

In physics, resonance is the tendency of a system to oscillate at a greater amplitude at some frequencies than at others. These are known as the system's resonant frequencies (or resonance frequencies) and are functions of the square root of the stiffness over the mass, the density of the material and the shape, including all dimensions. Since all diamonds have essentially identical densities (~3.5 g/cm$^3$), and single crystals have the same elastic constants (except when cracks are present), the shapes are significantly different—like snowflakes. Independent of how a resonance spectrum is created, it can be measured and compared with the archived fingerprint to observe whether or not it has been altered.

U.S. Pat. No. 5,922,956; "Dynamic Ultrasonic Resonant Testing, Rhodes, Jul. 13, 1999, describes a sample being excited by an exciting mechanical input (transducer) at a plurality of ultrasonic frequencies (the swept sine method), and sensing the resonant mechanical responses with the inverse process (1 or 2 mechanical receiving transducers). A dynamic signal analyzer is connected to receive the response of the sample and to output the resonance spectrum. A computer then determines the relevant resonances that adequately describe the conforming spectrum.

U.S. Pat. No. 5,495,763; Rhodes, et al. Mar. 5, 1996 entitled "Method for resonant measurement" first described the relevant resonance response characteristics of a sample being determined for use in characterizing the sample for non-destructive testing. In U.S. Pat. No. 5,062,296, Migliori described resonant ultrasound spectroscopy as a method to provide a unique characterization of an object for use in distinguishing similar objects having physical differences greater than a predetermined tolerance. Neither of these patents anticipated an application to diamonds, because it was not known that extraordinarily small dimensional and shape differences exist in samples that appear to be otherwise identical. Only experiments provided the complete picture. U.S. Pat. No. 9,304,112 describes the application of RUS to the detection of counterfeit gold bullion using gross elastic property differences. It was unknown whether the subtle dimensional differences in cut diamonds would allow the observation of fingerprint differences, as were subsequently shown by experiment.

U.S. Pat. Nos. 5,922,956, 5,495,763, 5,062,296 and 9,304,112 are hereby incorporated by reference in their entirety.

SUMMARY

The embodiments disclosed herein relate to the examination of diamonds, both cut/polished and rough, using the technology of Resonant Ultrasound Spectroscopy. The resonant frequencies are obtained by mechanically causing the stone to vibrate using a swept sine oscillator, sensing the resonance vibrations, and displaying the spectrum to yield a pattern describing the stone. The resonance fingerprints can be used to both track an individual stone to verify its integrity or to grade a rough stone to establish potential value.

The RUS spectrum is created by placing a stone on a fixture (FIG. 7) containing a transducer that broadcasts a swept sine, ultrasonically driving a mechanical excitation to the sample, and one or more identical transducers to detect the resonances produced. This process (FIG. 8), takes a few seconds to yield the signature. While there are hundreds of potential resonances that can be used, it is only useful to observe the absolute frequency, and the line shape Q (full width at half maximum, divided into the center frequency—Q) of a few, lowest frequency resonances to select those which provide the required diagnostic information. High Q resonances are those that have high values, therefore are narrow, and low Q broad, from which the quality, and center frequency accuracy, may be measured. All resonances are affected by geometry, including shape, and the elastic properties. Cut, polished diamonds are almost always single crystals (FIG. 1). Thus, the density and elastic properties are known values, and therefore the resonances are governed by the absolute geometry.

The rough stones will exhibit resonances if the crystal(s) contained are sufficiently large and insipient cracks are few. If too many cracks are present, the resonance spectrum lacks any detail.

This invention relates to the creation of resonances by connecting a frequency synthesizer (FIG. 8) to a piezoelectric material, causing that material to vibrate. The vibrating material (transducer) is placed into contact with the test sample, and the frequency synthesizer is stepped through a variety of frequencies which were previously determined to be in a range where distinct resonances could be observed. The test sample is also in contact with an additional, identical transducer, which senses the induced vibrations (resonances). The resulting signal is amplified and sent to a digital signal processor which may have the ability to examine both the in-phase and quadrature components of the signal. These data are easily processed in a computer to create a display of the resonance pattern.

This invention includes a method of examining diamonds, either cut and polished or rough, to obtain a digital frequency fingerprint comprising the steps of:

mounting the stone to be tested on an appropriate test stand;

contacting the stone by a minimum of two identical transducers without allowing any additional contacts that might dampen the resonance to be produced;

creating resonances in the stone by actively vibrating a piezoelectric transducer through a predetermined range of interest to produce resonances;

sensing the resultant resonances with a piezoelectric transducer;

amplifying the transducer signal sufficient to meet signal to noise requirements;

processing, in a computer with appropriate algorithms, the in phase and quadrature components of said resonance signal;

and displaying those data in a format where either a system, or human can make a judgment whether the test object has a useful resonance pattern (fingerprint) or not.

Spectra produced by the means described above, can easily be displayed for comparison by the human eye, or a computer algorithm. If an algorithm is used, some method to identify the absolute frequency is desired. There are several non-proprietary mathematical routines available for the purpose that have been applied in many industrial applications. Additionally, it is useful to display multiple spectra on a single graph, as is shown in FIG. 6. Here, 3 nearly identical 0.50 ct cut, round diamonds are fingerprinted and displayed. If a computer must accept, or reject samples based on spectral differences, the algorithms to be employed are trivial and easily developed.

While the invention has been described in conjunction with the specific exemplary embodiments thereof, it is evident that many alternatives, modifications, and variations will be apparent to those skilled in the art. Accordingly, embodiments of the invention as set forth herein are intended to be illustrative, not limiting. There are changes that may be made without departing from the spirit and scope of the invention.

DESCRIPTION OF THE DRAWINGS

FIG. 1 0.50 perfect diamond. Each of the 10 resonances between 1.5 MHz and 3.0 MHz show Q's of $10^4$.

Figure 1:
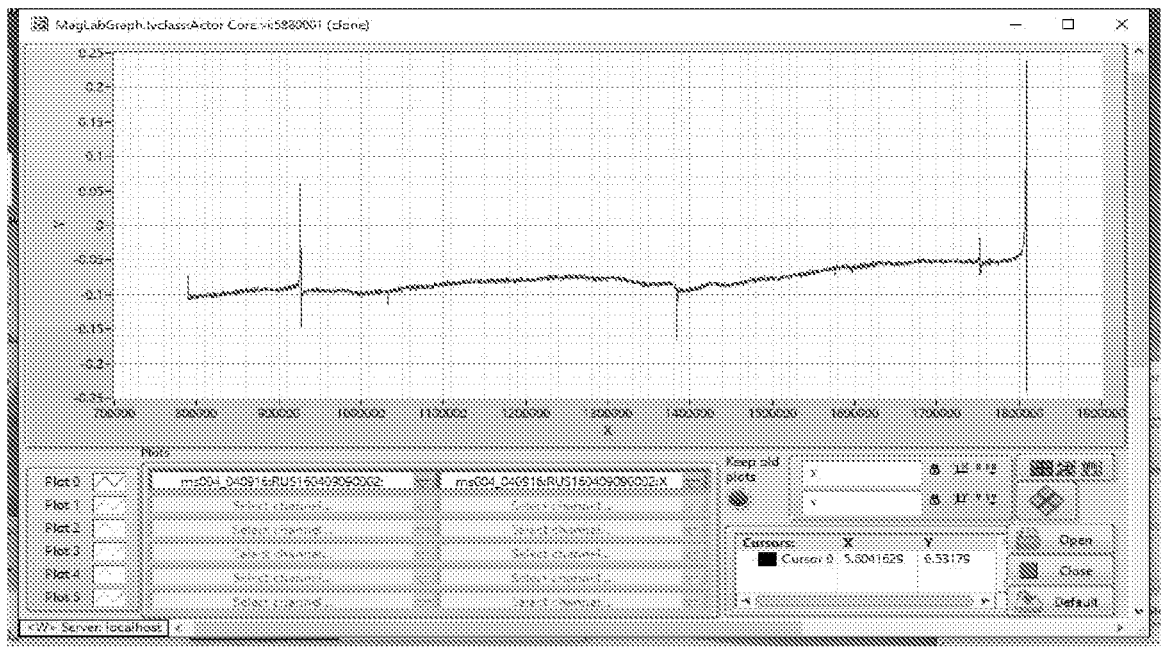
Figure 2:
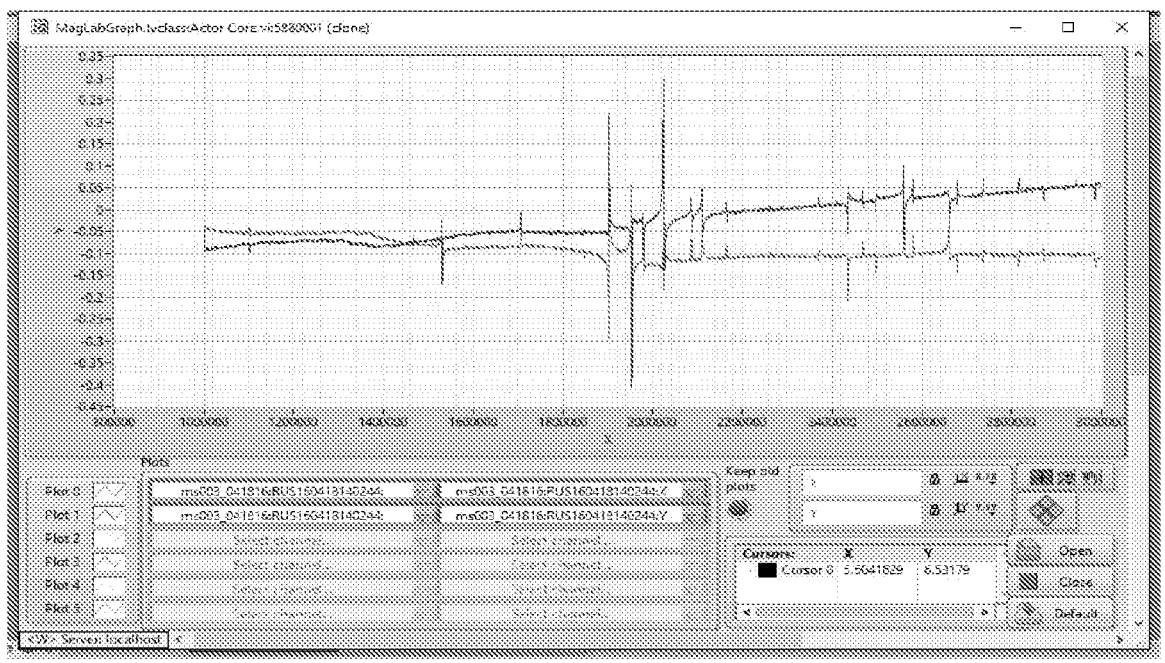
FIG. 2 shows a rough uncoated diamond, simple line shapes, high Q's are evident. Representative of gem quality with more than 1 crystal in the stone. Two traces are shown here corresponding to both the in-phase and quadrature components of the resonances.
Figure 3:
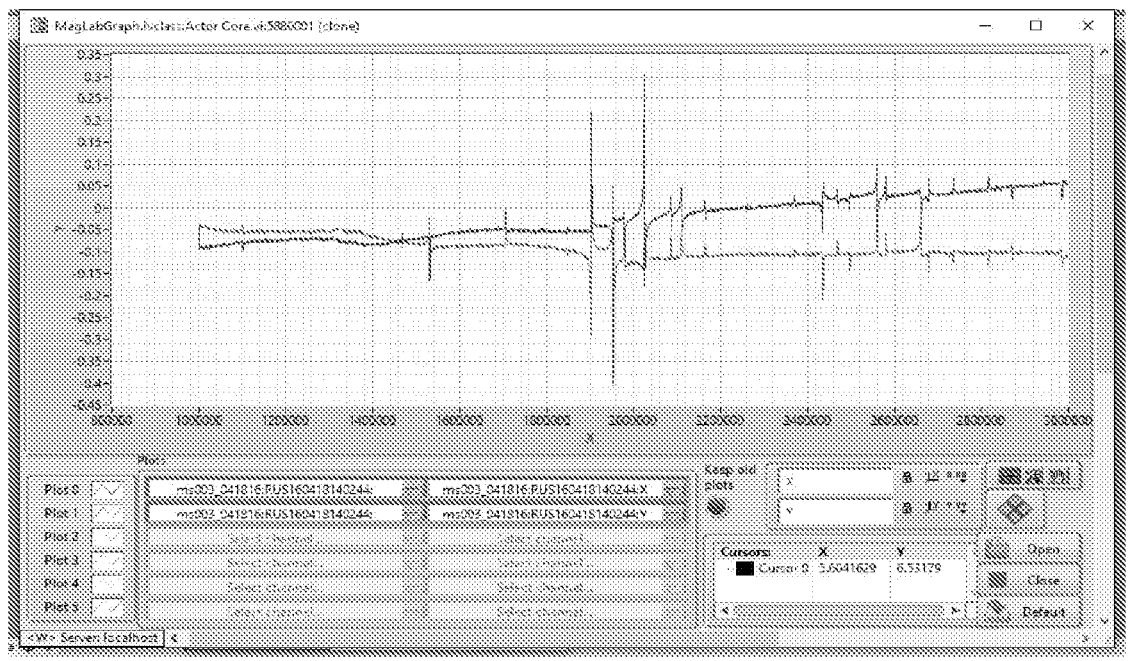
FIG. 3: shows a coated diamond of high quality, containing more than one crystal. These pictures illustrate the quality of the stone from the sharp resonances.
Figure 4:
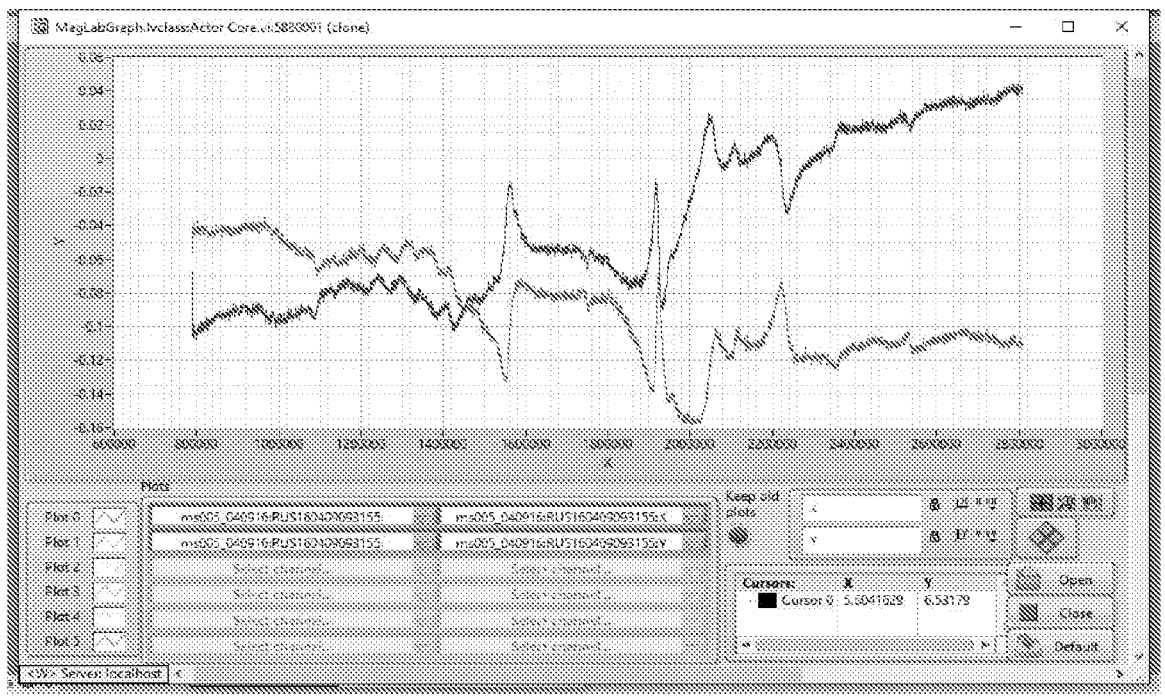
FIG. 4 shows a rough coated diamond indicating cracks, but with some identifiable resonances.
Figure 5:
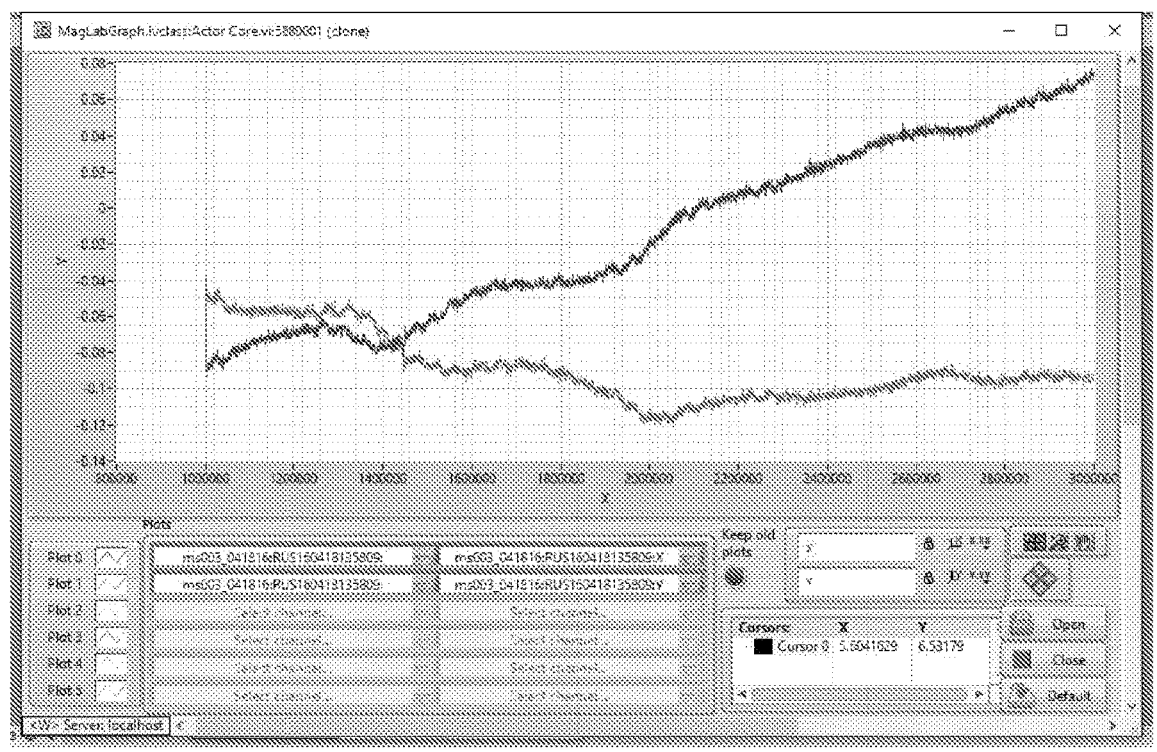
FIG. 5 shows a typical rough diamond with no discernable resonances.
Figure 6:
FIG. 6 illustrates the RUS testing of 3 nearly identical 0.50 ct samples to produce different patterns due to differences in geometries. The red, blue and green traces represent three different diamonds.
Figure 7:
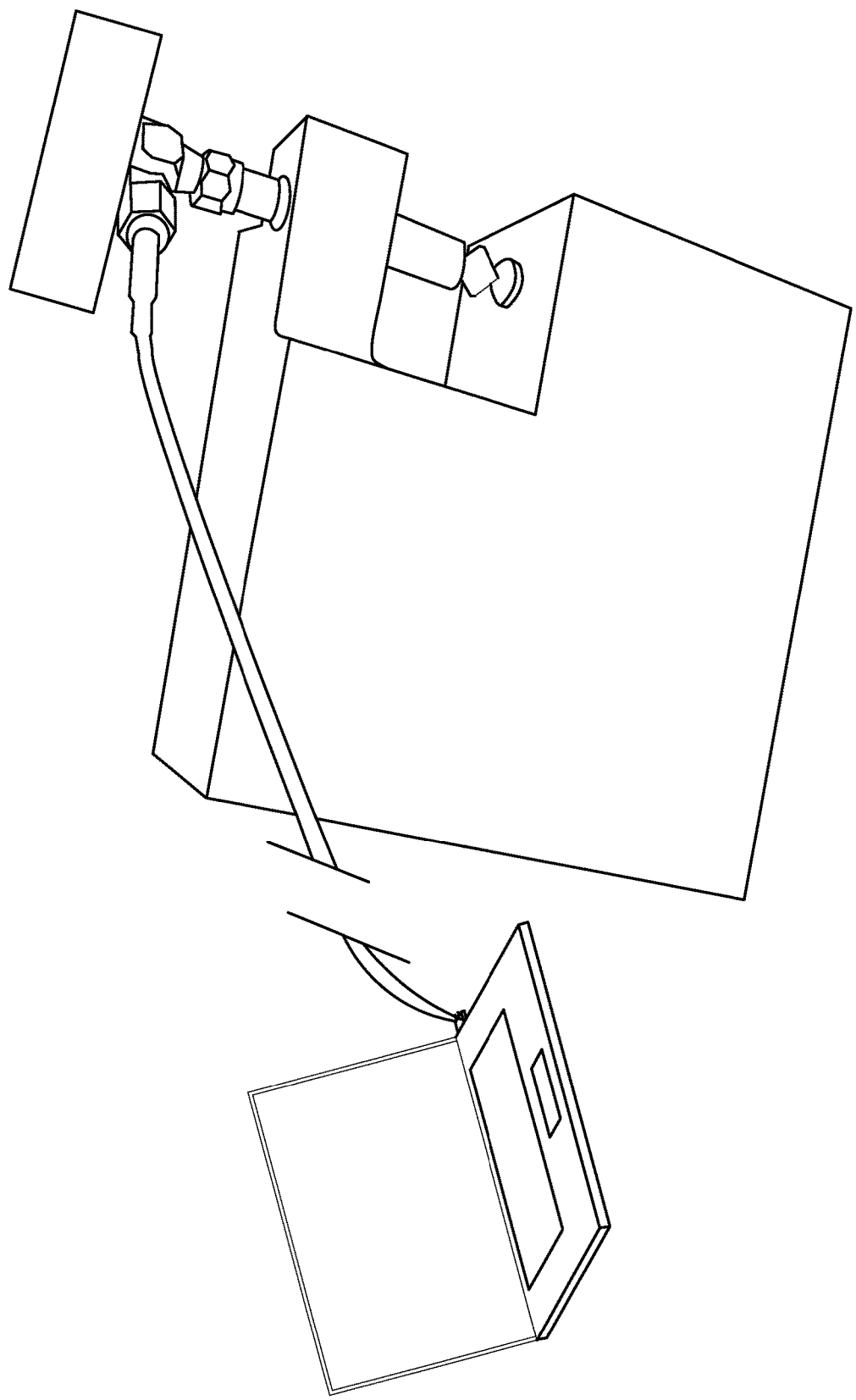
FIG. 7 shows a RUS sample mounting stage with diamond between the transducers.
Figure 8:
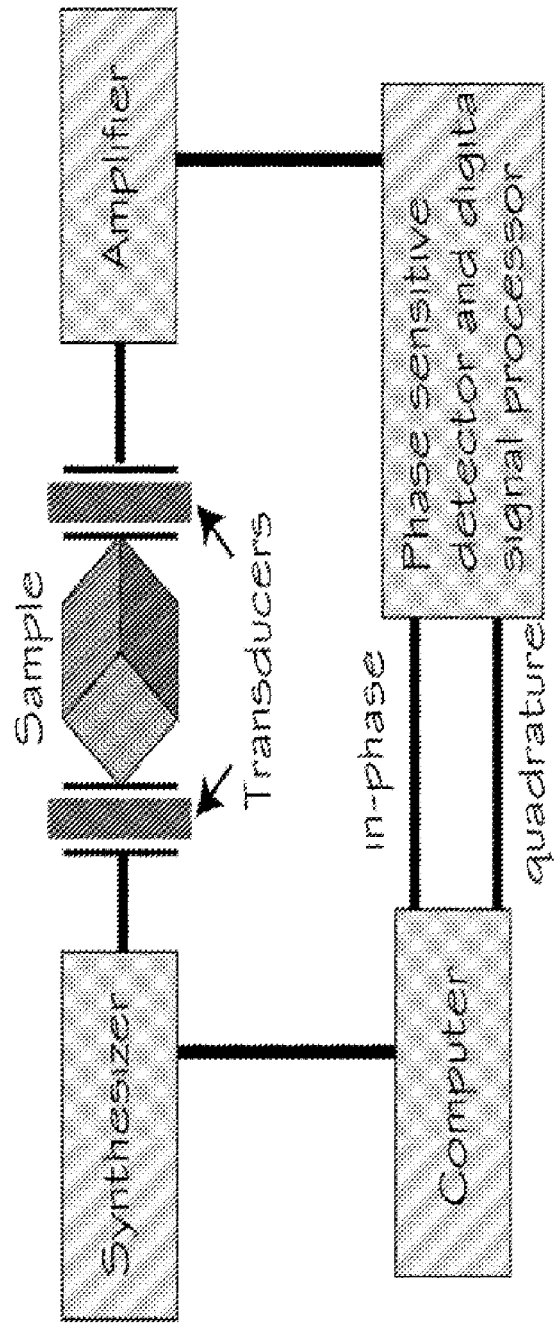
FIG. 8 shows a schematic diagram of a resonant ultrasound spectrometer. In all resonant ultrasound spectrometers a frequency synthesizer produces an electrical signal that is connected to a piezoelectric crystal, converting the electrical signal to a mechanical vibration. This mechanical transducer contacts a diamond causing it to vibrate. When a natural resonance of the material is found, the vibration occurs throughout the stone. An additional transducer (or 2) in contact with the stone, sense the resulting resonant mechanical displacement, creating an electrical signal which can be amplified, and processed to yield a display of the spectrum. These mechanical vibrations occur solely due to the dimensions, density and elastic properties of the stone. Since the density is nearly identical for all diamonds, whether cut and polished or rough, the resonances are controlled by the geometry and elastic properties.

What is claimed is:

1. A method of identifying a stone, the method comprising:
    by a computer in communication with a synthesizer, generating a first signal to send to the synthesizer,
        wherein the synthesizer is in communication with a first transducer,
        wherein the first transducer is in communication with the stone;
    by the computer in communication with a digital signal processor, receiving a second signal from the digital signal processor, wherein the second signal is received by the digital signal processor from a second transducer by an amplifier in communication with the digital signal processor,
        wherein the second transducer is in communication with the stone;
    by the computer, recording the received second signal from the digital signal processor;
    by the computer, stepping through additional signals by, generating a third signal to send to the synthesizer;
    by the computer, receiving a fourth signal from the digital signal processor, wherein the fourth signal is received by the digital signal processor from the second transducer by the amplifier in communication with the digital signal processor;
    by the computer, recording the received fourth signal from the digital signal processor;
    by the computer, determining a Q from the second received signal and the fourth received signal, wherein the Q is full width at half maximum, divided into a center frequency; and
    by the computer, combining the Q, the second received signal and the fourth received signal to generate a unique identifier for the stone.

2. The method of claim 1 wherein the second received signal and the fourth received signal are resonance signals of a stone in contact with the first transducer and the second transducer.

3. The method of claim 2 wherein the second resonance signals and fourth resonance signals are resonance ultrasound spectrum signals.

4. The method of claim 1 wherein the second received signal and the fourth received signal from the digital signal processor includes an in-phase signal and a quadrature signal.

5. The method of claim 1 wherein the first signal and the third signal are signals to induce a spectrum of resonance ultrasound signals.

6. The method of claim 1 wherein the digital signal processor includes a phase sensitive detector.

7. The method of claim 1 wherein the first transducer and the second transducer are both piezoelectric mechanical transducers.

8. The method of claim 1 further comprising, by the computer, causing display of resulting received second signal and received fourth signal.

9. The method of claim 1, further comprising, by the computer, determining the number of crystals in the stone, by analysis of the second received signal.

10. A non-transitory computer-readable medium having computer-executable instructions thereon for a method of identifying a stone, the method comprising:
    by a computer in communication with a synthesizer, generating a first output signal to send to the synthesizer,
        wherein the synthesizer is in communication with a first transducer,
        wherein the first transducer is in communication with the stone;
    by the computer in communication with a digital signal processor, receiving a first input signal from the digital signal processor, wherein the second signal is received by the digital signal processor from an amplifier in communication with the digital signal processor, and
        wherein the amplifier is in communication with a second transducer,
        wherein the second transducer is in communication with the stone,
        and wherein the received first output signal is a resonance signal a stone in contact with the first transducer and the second transducer;
    by the computer, causing storage of the received first input signal from the digital signal processor;
    by the computer, stepping through additional signals by, generating a second output signal to send to the synthesizer;
    by the computer, receiving a second input signal from the digital signal processor, wherein the second input signal is received by the digital signal processor from the second transducer by the amplifier in communication with the digital signal processor, wherein the received second output signal is a resonance signal a stone in contact with the first transducer and the second transducer;
    by the computer, causing storage of the received second input signal from the digital signal processor;
    by the computer, comparing the received first input signal and the received second input signal to determine a match;
    by the computer, determining a Q from the first received input signal and the second received input signal, wherein the Q is full width at half maximum, divided into a center frequency; and
    by the computer, combining the Q, the second received signal and the fourth received signal to generate a unique identifier for the stone.

11. The non-transitory computer-readable medium of claim 10 the method further comprising, by the computer, determining a Q from the first received input signal and the second received input signal, wherein the Q is full width at half maximum, divided into a center frequency.

12. The non-transitory computer-readable medium of claim 10 the method further comprising, by the computer, determining the number of crystals in the stone, by analysis of the second received signal.

13. The non-transitory computer-readable medium of claim 10 the method further comprising, by the computer, determining inclusions in the stone, by analysis of the second received signal.

14. The non-transitory computer-readable medium of claim 10 the method further comprising, by the computer, determining dimensions of the stone, by analysis of the second received signal.

15. The non-transitory computer-readable medium of claim 10 the method further comprising, by the computer, determining shape of the stone, by analysis of the second received signal.

* * * * *